(12) United States Patent
Grundei

(10) Patent No.: US 6,641,616 B1
(45) Date of Patent: Nov. 4, 2003

(54) HOLLOW ENDOPROSTHESIS

(75) Inventor: Hans Grundei, Lübeck (DE)

(73) Assignee: Eska Implants GmbH & Co. (DE)

( * ) Notice: Subject to any disclaimer, the term of this patent is extended or adjusted under 35 U.S.C. 154(b) by 0 days.

(21) Appl. No.: 09/913,633

(22) PCT Filed: Feb. 2, 2000

(86) PCT No.: PCT/EP00/00842

§ 371 (c)(1),
(2), (4) Date: Jan. 8, 2002

(87) PCT Pub. No.: WO00/48534

PCT Pub. Date: Aug. 24, 2000

(30) Foreign Application Priority Data

Feb. 16, 1999 (DE) .......................... 199 07 489

(51) Int. Cl.[7] .................................................. A61F 2/36
(52) U.S. Cl. .................................................. 623/23.26
(58) Field of Search .......................... 623/11.11, 16.11, 623/22.11, 23.15, 23.26, 23.29, 23.3, 23.31, 23.33, 23.44, 23.64

(56) References Cited

U.S. PATENT DOCUMENTS

| 4,089,071 | A | * | 5/1978 | Kalnberz et al. | ........ | 623/23.61 |
| 4,938,772 | A | * | 7/1990 | Frey et al. | ................ | 623/23.28 |
| 5,433,750 | A | * | 7/1995 | Gradinger et al. | ....... | 623/23.54 |
| 5,443,510 | A | * | 8/1995 | Shetty et al. | ................... | 419/2 |
| 5,824,043 | A | * | 10/1998 | Cottone, Jr. | ................ | 623/1.13 |
| 6,287,342 | B1 | * | 9/2001 | Copf et al. | .............. | 623/16.11 |

FOREIGN PATENT DOCUMENTS

| CH | 674928 | 7/1988 |
| DE | 29 25 371 | 1/1980 |
| DE | 37 38 045 | 6/1988 |
| DE | 41 06 971 | 3/1992 |
| DE | 41 05 165 | 8/1992 |
| DE | 195 43 530 | 5/1997 |
| FR | 2 744 010 | 8/1997 |
| WO | WO 98 26725 | 6/1998 |

* cited by examiner

Primary Examiner—Eduardo C. Robert
(74) Attorney, Agent, or Firm—Cantor Colburn LLP

(57) ABSTRACT

A hollow endoprosthesis including a metal grid network, metal particles mounted at least at junctions of the metal grid network, and a solid metal portion. Each of the metal particles includes a basic body and at least three pins projecting radially from the basic body, and is an integral part of a material forming the grid network.

10 Claims, 2 Drawing Sheets

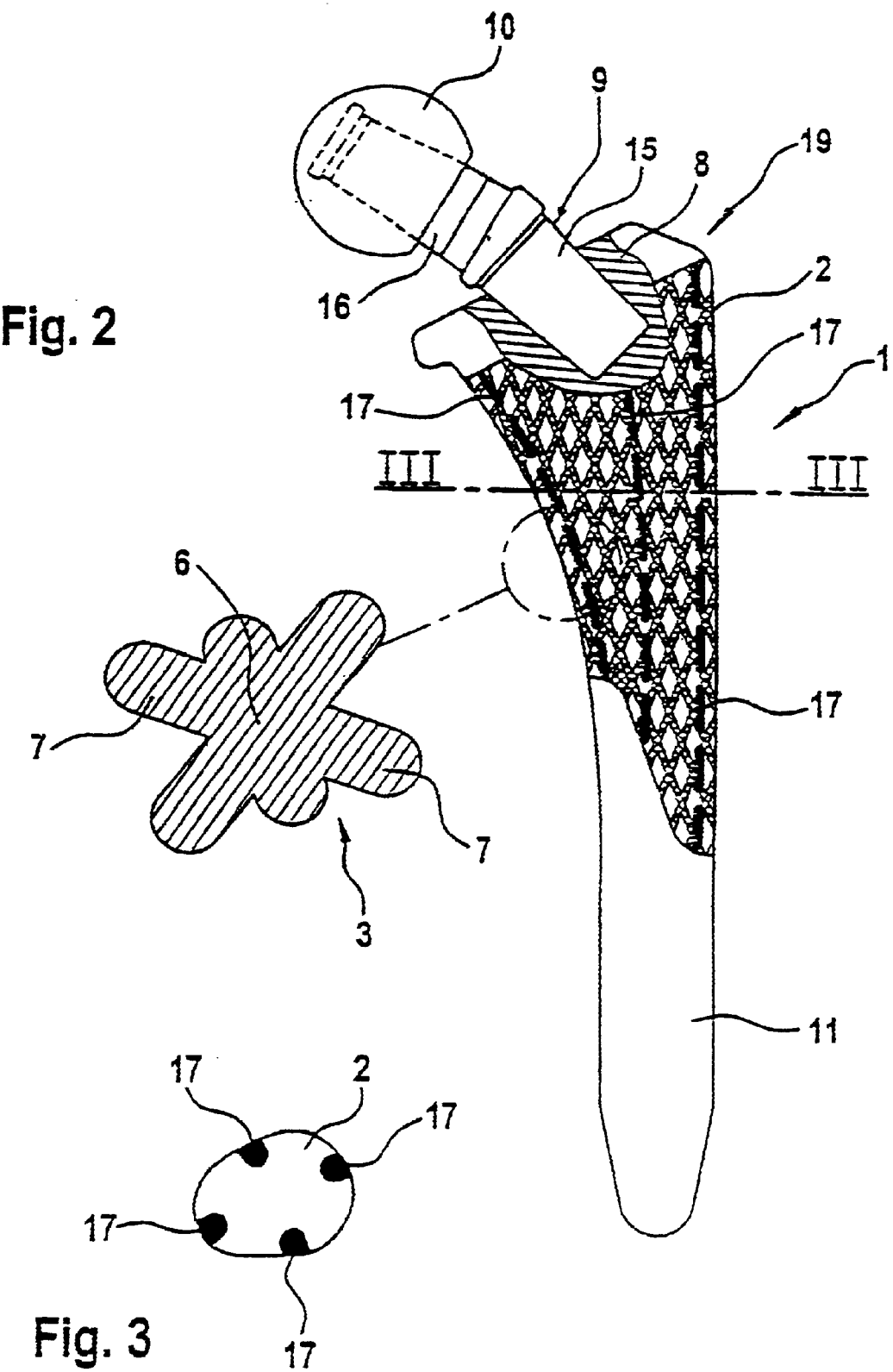

HOLLOW ENDOPROSTHESIS

FIELD OF THE INVENTION

This invention concerns a hollow endoprosthesis for use in a tubular bone.

Endoprostheses for use in a tubular bone have been known for a long time in many designs. They are set in the bones surgically after the medullary space is routed out and are anchored there either without cement or with bone cement.

DESCRIPTION OF THE RELATED ART

This invention concerns an endoprosthesis in the first class mentioned, i.e., an endoprosthesis that can be fixed in tubular bones without cement. A number of different implants are also known from this class. The only examples referred to here are implants that are produced by the method described in DE-A-41 06 971. Variations are described in DE-A-195 43 530, for example. The implants mentioned are characterized by the fact that they basically have a basic solid metal body, which is covered, at least partly, by a three-dimensional, open-mesh spatial network structure, into which and through which bone material of the bone tissue surrounding the implant grows after implantation to achieve a permanent secondary fixation of the implant in the tubular bone.

These known implants have major advantages compared to implants fixed with cement. Thus, after complete organization at a number of bone trabeculae, the implant is embedded almost hanging free in the surrounding spongiosa, so it can make stress-dependent equalizing movements in the medullary space, but this is not possible in practice for an implant that is cemented in, since then discrete layers (bone-cement implant) hit and work against one another. In this case, the layer of bone cement that connects the implant is on the layer of spongiosa. Equalizing movements under stress cause loosening of the bone cement and hence loosening of the seat of the implant in the bone.

But there can also be problems with the implants fixed without cement described due to the solidity of the basic body, because the implants, on one hand, and the bone, on the other, have very different moduluses of electricity. Thus, the modulus of electricity of the implant is much higher than that of the bone, which, despite the favorable free suspension in the spongiosa, can lead to problems with the loosening of the implant.

SUMMARY OF THE INVENTION

On this background, it is the purpose of this invention to propose an implant which has much less of a tendency to be loosened in its seat in tubular bones.

This purpose is accomplished, in general, with a hollow endoprosthesis, which consists mainly of a metal grid network, which has metal particles at least at its junctions, which is made of a basic body and at least three pins projecting radially from it which are integral parts of the material forming the grid network, and part of which is also composed of solid metal.

The design as a hollow implant by the grid network causes a significant adaptation of the modulus of electricity of the endoprosthesis and of the bone.

In other words, despite its load-bearing structure, the implant is given a certain elasticity which allows it to react in a quasi-bone-like way to the stresses that occur.

Metal particles are used to stimulate the growth of the bone material surrounding the endoprosthesis, and they give the endoprosthesis an aggressive exterior, whereby the surrounding bone material is stimulated to bleed and thus to build and organize bone trabeculae into the structures.

To maintain sufficient stability of the endoprosthesis, it is provided that part consist of solid metal, but a smaller part than out of the grid network. This other solid part assumes a guide function for the endoprosthesis, in the area where only small forces must be introduced from the endoprosthesis into the bone material. If the hollow endoprosthesis in the invention is designed as a hip shaft of an artificial hip joint, the solid part made of metal forms the distal end of the hip shaft.

It is especially preferred if at least 60% of it is composed of the metal grid network. Accordingly, the remaining 40% is solid, and in the case of a hip shaft, on the distal part and to a smaller degree in the proximal area for coupling an artificial joint cavity. This endoprosthesis therefore has at least a 60% area in which the corresponding modulus of electricity approximates that of the bone.

To increase mechanical stability while only slightly increasing the modulus of electricity of the section of the endoprosthesis consisting of the grid network, it may an advantage to provide reinforcing braces made with the grid network. In the case of a hip shaft prosthesis, for example, they would run parallel from proximal to distal to the solid metal distal section.

In summary, it should once more be emphasized that designing a large part of the endoprosthesis as a metal grid network is essential in terms of equalizing the modulus of electricity, and mounting it with the particles described is essential in terms of stimulating the growth of the bone material surrounding the endoprosthesis for fast, permanent organization in and through the plane of the surface structure, which is made of particles and then into the inside of the endoprosthesis.

BRIEF DESCRIPTION OF THE DRAWINGS

The invention will be described in greater detail using two examples of embodiment.

FIG. 2 shows a similar view of the hip shaft in FIG. 1 in an altered embodiment, and FIG. 3 shows a sectional view along line III—III in FIG. 2.

DETAILED DESCRIPTION OF THE PREFERRED EMBODIMENT

Figure 1:
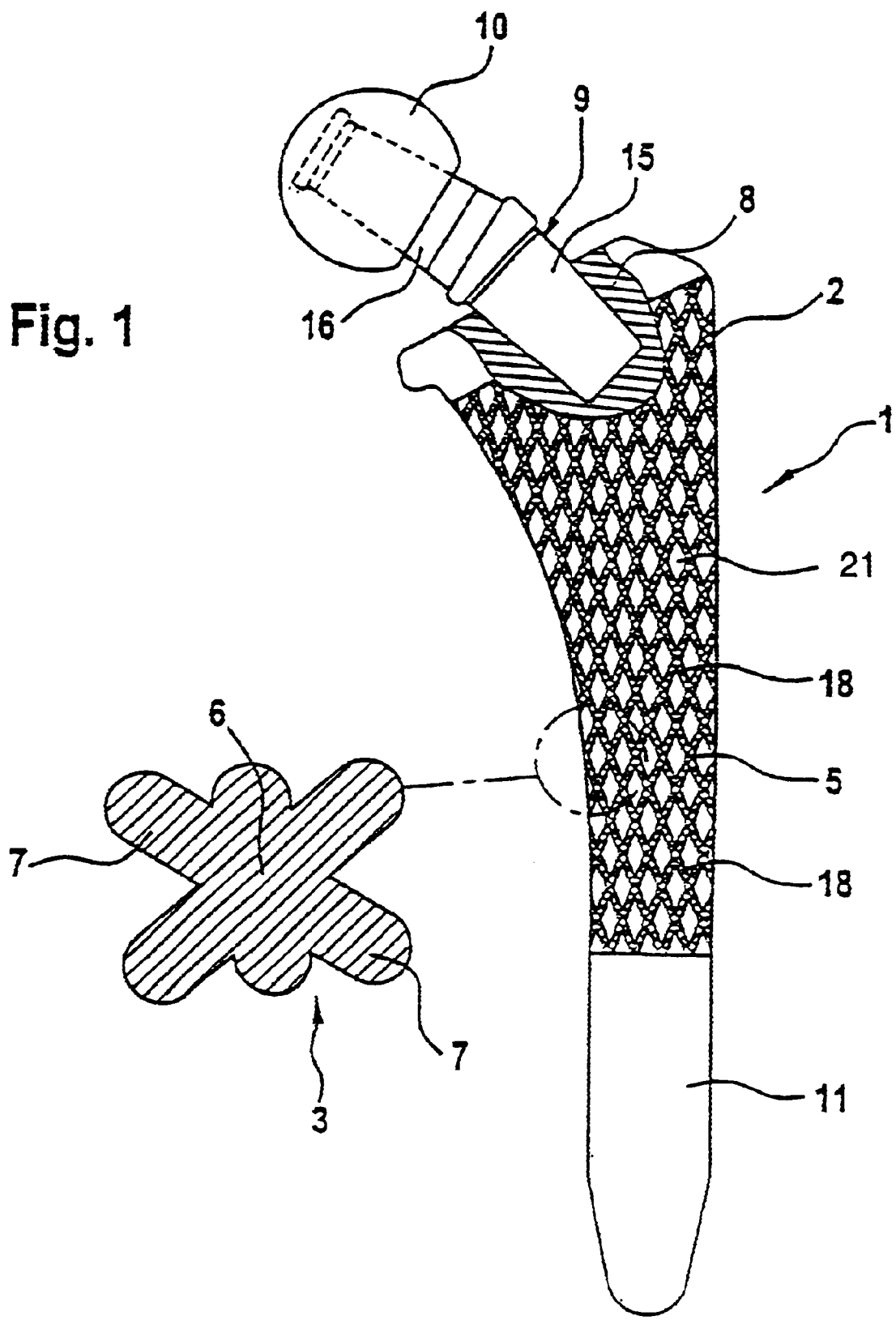
FIG. 1 shows a hollow endoprosthesis in designed as a hip shaft of an artificial hip joint with particles, shown enlarged, on the outside of the grid network.

The same reference numbers and letters are used to mark the same parts below.

FIG. 1 shows a partial section of a hip joint, hence the femur part of an artificial hip joint.

The hip shaft 1 has an artificial head 10 of the hip joint, which is connected by means of a double cone adapter 9 to insertion cones 15 and 16 to the solid connecting part 8 of the hip shaft 1 with a receptacle.

The hip shaft 1 mainly consists of a metal grid network 2 with open mesh 21 between the pins 18 forming the grid network 2.

At least at the junctions 5, where the pins 18 cross, metal particles 3 are provided. They are made integral with the grid network 2, preferably cast in a fine-casting wax-melting method with the grid network.

The sectional enlargement shows particle 3 more clearly. It is composed of a basic body 6 and pins 7 projecting radially from it. This design gives the surface of the hollow endoprosthesis enormous aggressiveness compared to the bone material surrounding it after implantation in the femur. This mechanical aggressiveness substantially promotes the growth of the bone trabeculae.

The distal part of the hip shaft 1 here is designed as a solid part 11, which performs a guide function for the endoprosthesis. This guide function centers the hip shaft in the medullary space of the femur.

The hollow endoprosthesis shown in FIG. 2 is different from the one in FIG. 1 in terms of two features. Therefore the following will mainly concentrate on these different features:

In the form of embodiment shown, reinforcing braces 17 are provided, which run from the proximal end 19 of the hip shaft 1 to the distal solid part 11. Their arrangement on the grid network 2 is shown in FIG. 3, which shows a schematic section along line III—III in FIG. 2. It can be seen how each reinforcing brace 17 runs in the medial, lateral, dorsal and ventral area of the hip shaft 1. This compensates for structurally-induced insufficient stability of the grid network 2, whereby the modulus of electricity is also approximated to the modulus of electricity of the bone.

The overall result is fast growth behavior of the hollow endoprosthesis because of the enormous mechanical aggressiveness of its outer structure in the area of the grid network 2 and high long-term stability because of the design of the overwhelming part as a grid network 2 due to the then approximated values of the modulus of electricity of the endoprosthesis and the bone.

What is claimed is:

1. A hollow endoprosthesis comprising: a metal grid network; metal particles mounted at least at junctions of the metal grid network; and a solid metal portion; wherein each of the metal particles includes a basic body and at least three pins projecting radially from the basic body, the metal particles being an integral part of a material forming the grid network.

2. The hollow endoprosthesis in claim 1, wherein the metal grid network forms at least 60% of the hollow endoprosthesis.

3. The hollow endoprosthesis in claim 2, wherein the hollow endoprosthesis is a hip shaft endoprosthesis and the solid metal portion forms a distal end of the hip shaft.

4. The hollow endoprosthesis in claim 2, further comprising a plurality of reinforcing braces made in one-piece with the grid network.

5. The hollow endoprosthesis in claim 1, wherein the hollow endoprosthesis is a hip shaft endoprosthesis and the solid metal portion forms a distal end of the hip shaft.

6. The hollow endoprosthesis in claim 5, further comprising a plurality of reinforcing braces made in one-piece with thd grid network.

7. The hollow endoprosthesis in claim 6, wherein the reinforcing braces run from a proximal end to the solid metal portion.

8. The hollow endoprosthesis in claim 1, further comprising a plurality of reinforcing braces made in one-piece with the grid network.

9. The hollow endoprosthesis in claim 8, wherein the reinforcing braces run from a proximal end to the solid metal portion.

10. The hollow endoprosthesis in claim 9, wherein the metal solid portion forms a distal end of the endoprosthesis.

* * * * *